(12) United States Patent
Rath et al.

(10) Patent No.: US 8,003,110 B1
(45) Date of Patent: Aug. 23, 2011

(54) METALLOPROTEINASE OLIGOPEPTIDES AND THEIR THERAPEUTIC USE

(75) Inventors: Matthias W Rath, Aptos, CA (US); Aleksandra Niedzwiecki, Aptos, CA (US); Waheed M Roomi, Sunnyvale, CA (US)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 13/012,769

(22) Filed: Jan. 24, 2011

(51) Int. Cl.
*A61K 39/00* (2006.01)

(52) U.S. Cl. ............... 424/185.1; 424/192.1; 424/193.1; 424/277.1; 530/326; 530/328; 530/350

(58) Field of Classification Search .................. 530/326, 530/328, 350; 424/185.1, 192.1, 193.1, 277.1
See application file for complete search history.

(56) References Cited

FOREIGN PATENT DOCUMENTS
WO   WO 2004/110477 A1 * 12/2004

OTHER PUBLICATIONS

Wang et al. (Surgery. Aug. 2002; 132 (2): 220-5).*

* cited by examiner

*Primary Examiner* — Stephen Rawlings
(74) *Attorney, Agent, or Firm* — Geeta Kadambi; Riddhi IP LLC

(57) ABSTRACT

The invention discloses identification and therapeutic use of matrix metalloproteinase oligopeptides and peptidomimetics. The oligopeptides are used for making antibodies. The antibodies are used for diagnostic and treatment purposes of various diseases. In particular, the diseases may involve the mechanism of degradation of extracellular matrix by MMP's during cell proliferation cycle. Suppression of MMP activity seems to arrest tumor growth during cancer progression. MMP oligopeptides were used as vaccines to treat mice having murine melanoma B16FO induced tumor. There was a significant drop in tumor weight and size for the group of mice that were immunized with MMP oligopeptide.

15 Claims, 15 Drawing Sheets

HELA: CONTROL

HELA: MMP-9, A 1 1:100

HELA: CONTROL

HELA: MMP-9, A 2 1:100

HELA: CONTROL

HELA: MMP-9, A 3 1:100

HELA: CONTROL

HELA: MMP-9, A 4  1:100

Inhibition of tumor weight in mice immunized with tested oligopeptides

Inhibition of tumor burden in mice immunized with tested oligopeptides

CONTROL TUMOR

TREATED TUMOR MMP-9 A 1

TREATED TUMOR MMP-9 A 2

TREATED TUMOR MMP-9 A 3

TREATED TUMOR MMP-2 A 4

A. Three Dimensional Structure of Entire Metalloproteinase 9 (MMP-9) Molecule

B. 3D Structure of MMP 9 Peptide designated A3

C. 3D Structure of MMP 9 Peptide designated A2

D. 3D Structure of MMP 9 Peptide designated A1

SEQUENCE LISTING

```
<160> NUMBER OF SEQ ID NOS: 4

<210> SEQ ID NO 1
<211> LENGTH: 10
<212> TYPE: PRT
<213> ORGANISM: Artificial Sequence
<220> FEATURE:
<223> OTHER INFORMATION: Synthetic Oligopeptide Sequence

<400> SEQUENCE: 1

Cys Pro Arg Lys Pro Lys Trp Asp Lys Cys
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic Oligopeptide Sequence

<400> SEQUENCE: 2

Cys His Phe Pro Phe Ile Phe Glu Gly Arg Ser Tyr Ser Ala Cys
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Synthetic Oligopeptide Sequence

<400> SEQUENCE: 3

Asp Thr Asp Asp Arg Phe Gly Phe
```

```
-continued

<210> SEQ ID NO 4
<211> LENGTH: 15
<212> TYPE: PRT
<213> ORGANISM: Artificial Sequence
<220> FEATURE:
<223> OTHER INFORMATION: Synthetic Oligopeptide Sequence

<400> SEQUENCE: 4

Asp Arg Asp Lys Leu Phe Gly Phe Cys Pro Thr Arg Ala Asp Ser
1               5                   10                  15
```

METALLOPROTEINASE OLIGOPEPTIDES AND THEIR THERAPEUTIC USE

This application contains sequence listing that has been submitted as an ASCII file named RIPLLC018.003US1sequence_ST25.txt, the date of creation Apr. 18, 2011, and the size of the ASCII text file in bytes is 2 kb.

FIELD OF TECHNOLOGY

This disclosure relates generally to designing and synthesizing novel metalloproteinase oligopeptide sequences to be used as therapeutic agents for treating extracellular matrix related diseases. More specifically, this disclosure relates to using the metalloproteinase oligopeptide as a vaccine and/or peptidomimetics to treat cancer.

BACKGROUND

Matrix Metalloproteinases are a family of zinc dependent neutral endopeptidases that play an important role in tumor angiogenesis, tissue remodeling, and cell migration. In cancer, levels of some MMP's are abnormally elevated, enabling cancer cells to degrade the extracellular matrix (ECM), invade the vascular basement membrane, and metastasize to distant sites. A variety of pathological conditions are associated with an increased activity of metalloproteinases (MMP's), in particular MMP-2 and MMP-9. These proteases are able to digest collagen and other extracellular matrix (ECM) proteins as a precondition for the spreading of the disease. Thus, there is a need for a therapeutic agent to effectively block these MMP's from digesting the ECM, thereby blocking the spread of cancer and other diseases.

Prevention and treatment of metastasis represents the major challenge in cancer therapy today. The current available treatments are toxic, non-specific and unpredictable for ECM protein affected diseases. There is a need for a therapeutic agent to effectively block the MMP molecules from digesting the ECM, thereby preventing ECM degradation and spreading of diseases.

SUMMARY

The current disclosure discloses a sequence and a composition of MMP oligopeptide and a method of using the MMP oligopeptide as a vaccine and a peptidomimetic for treating ECM related diseases.

In one embodiment, the oligopeptide analogs for MMP-9 and MMP-2 sequences were designed and synthesized. In another embodiment, these oligopeptides were tested for their ability to inhibit cancer cell invasion in-vitro using specific cell lines.

In another embodiment, the oligopeptide analogs of MMP-9 and MMP-2 were tested for their effectiveness for tumor growth suppression in-vivo in mice.

In one embodiment, the following oligopeptide sequences were used to produce a vaccine.

```
MMP-9    Oligopeptides
MMP-9    A1: -C-H-F-P-F-I-F-E-G-R-S-    (SEQ ID NO: 2)
             Y-S-A-C-

MMP-9    A2: -D-T-D-D-R-F-G-F-          (SEQ ID NO: 3)

MMP-9    A3: -D-R-D-K-L-F-G-F-C-P-T-    (SEQ ID NO: 4)
             R-A-D-S-

MMP-2    Oligopeptide
MMP-2    A4: -C-P-R-K-P-K-W-D-K-C       (SEQ ID NO: 1)
```

In one embodiment, the sequence of oligopeptide may but is not limited to have mutations, deletions and substitutions.

In one embodiment, the MMP-2 oligopeptide may be used as a vaccine and/or a peptidomimetic. In another embodiment, MMP-9 oligopeptide may be used in combination with any one of the MMP-2 oligopeptides as a vaccine. In another embodiment, all four oligopeptide may be combined to produce a vaccine.

The oligopeptide sequences, in one embodiment may be either linear or circular in design. In another embodiment, the oligopeptide may repeat of sequences.

In another embodiment, the oligopeptide may have either haptens or polyglycans attached to them for efficient delivery.

In another embodiment, a method of immunizing a mammal, such as mice, to raise antibodies for a specific MMP is disclosed. In one embodiment, a selection of an oligopeptide suitable for raising antigenicity is disclosed. In another embodiment, inhibition of cancer cell invasion by oligopeptide induced antibody in-vitro was performed.

In another embodiment, mammals such as mice may be immunized and were subsequently challenged with murine melanoma cancer cells B16F0 in order to test the inhibition of tumor growth.

In one embodiment, the immunization of mammals may not be limited to cancer but may include all ECM degradation based disease treatment. In another embodiment, the vaccination may be done once or repeatedly by measuring the antibodies specific to the oligopeptide that was injected.

In one embodiment, a composition for an oligopeptide as a vaccine and peptidomimetic comprising of oligopeptide MMP-9 A1, MMP-9 A2, MMP-9 A3 and MMP-2 A4 individually or combination thereof.

In one embodiment the therapeutically effective amount may be rendered, but not limited to, as an injection. Other embodiments may include peroral, topical, transmucosal, inhalation, targeted delivery and sustained release formulations.

The composition, method, and treatment disclosed herein may be implemented in any means for achieving various aspects, and may be executed in a form suitable for the mammal. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Several sequences and methods for immunizing, treating cancer and reducing the size of the tumor using the matrix metalloproteinase oligopeptide as a vaccine are described herein. Although the present embodiments have been described with reference to specific example embodiments, it will be evident that various modifications and changes may be made to these embodiments without departing from the broader spirit and scope of the various embodiments.

Figure 1:
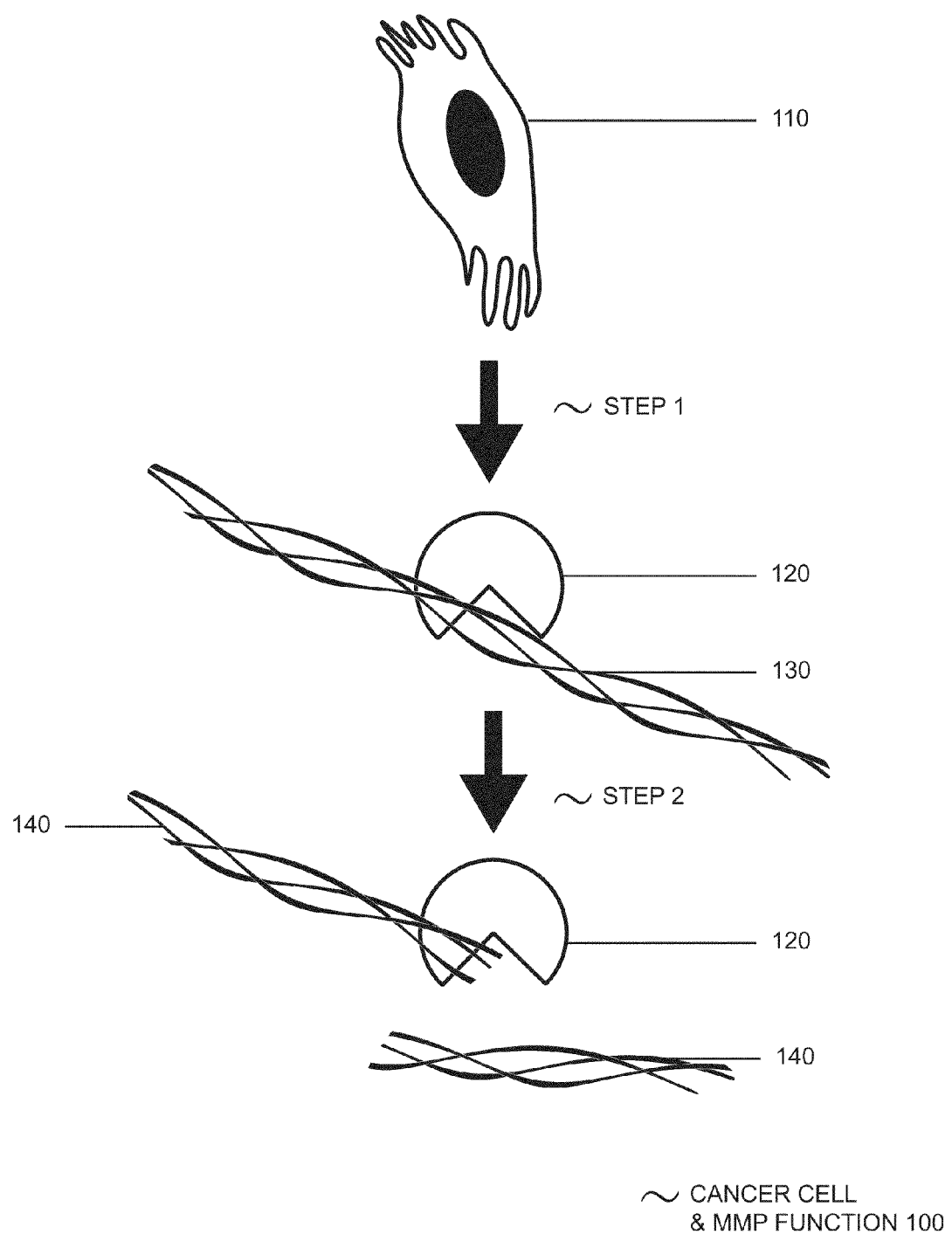
FIG. 1 illustrates the prior art of MMP's digesting the ECM during a disease state.

Cancer cells produce higher levels of matrix metalloproteinases (MMP's), particularly MMP-9 and MMP-9. These enzymes are able to digest the extra cellular matrix (ECM) connective tissue surrounding the cancerous cells. MMP's bind to ECM via specific binding sites. Blocking these binding sites in the MMP's prevents the MMP's from binding to ECM. Inhibition of ECM destruction prevents the cancer progression and tumor size reduction. In the current disclosure several potential binding sites were identified within MMP-9 and MMP-2. FIG. 1 describes the cancerous cells 110 producing MMP's 120 (step 1). The MMP's 120 bind to the specific binding sites at the ECM 130 (step 2). Step 3 in FIG. 1 shows the MMP's 120 digesting the ECM 140.

Figure 2:
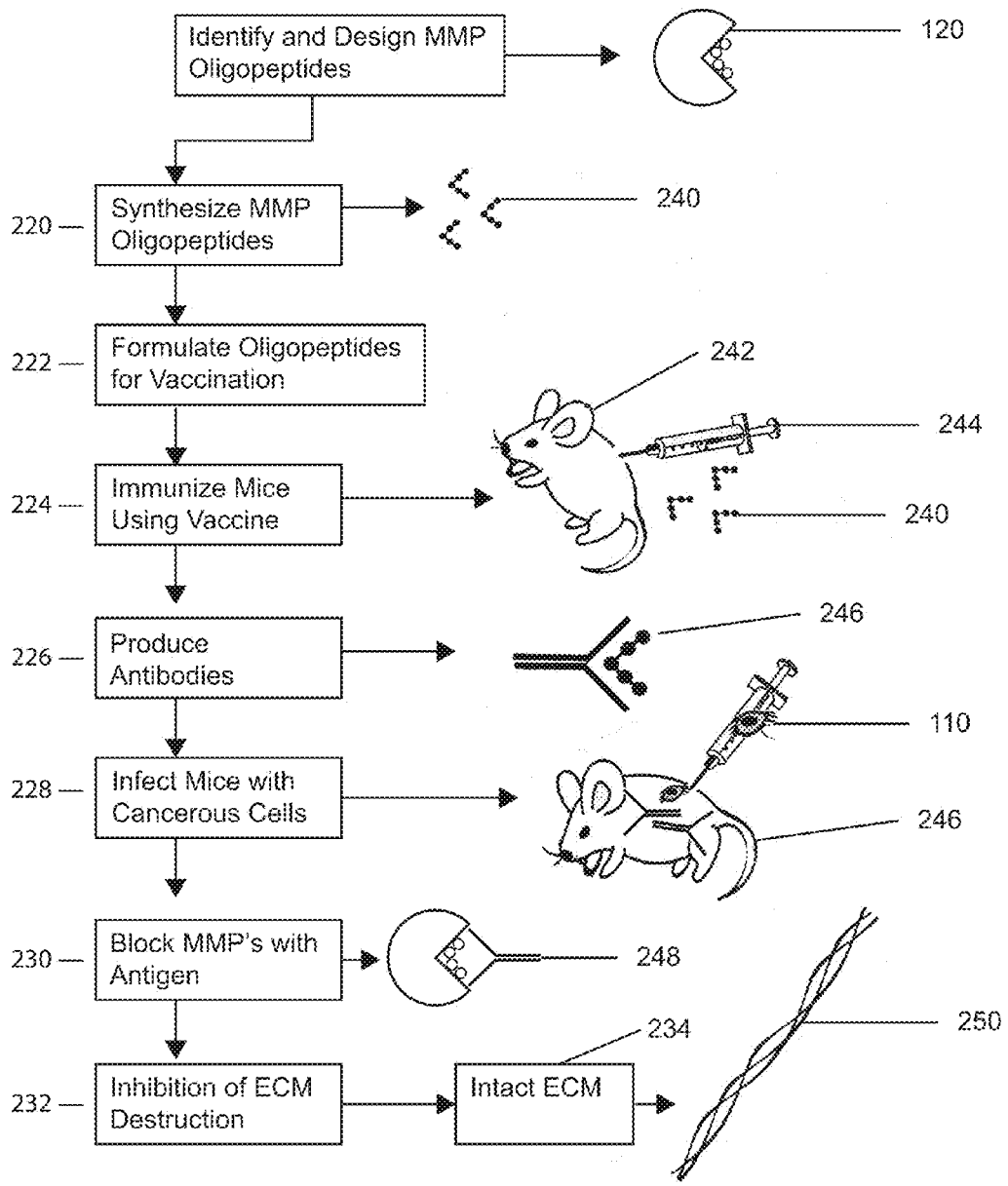
FIG. 2 the method of treating a mammal using the vaccine.
Figure 3A:
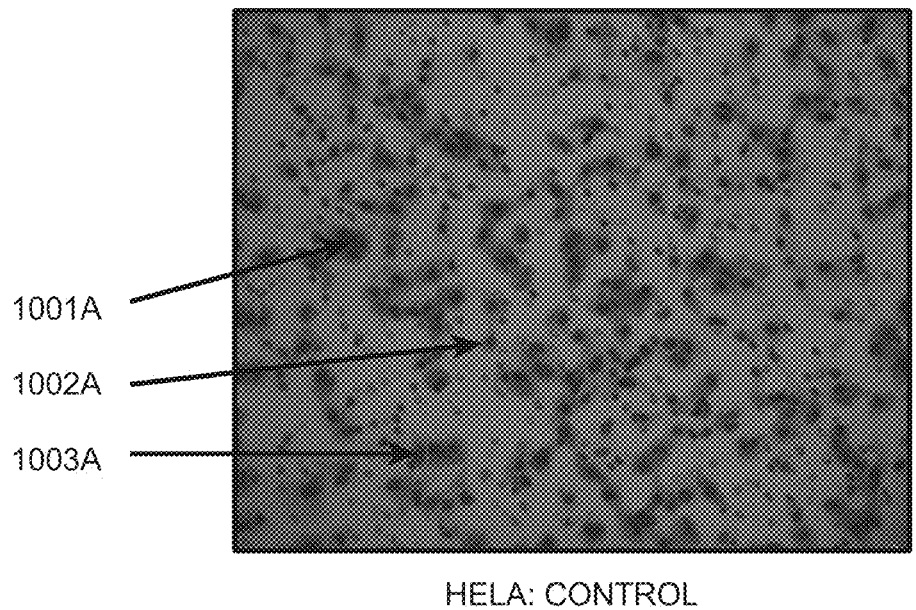
FIG. 3 A-D shows the view of the matrigel invasion experiment in HeLa control cells as well as HeLa cervix cancer cells and the effect of immune sera from matrix metalloproteinase oligopeptide MMP-9 A 1-3 and MMP-2 A4.
Figure 3A:
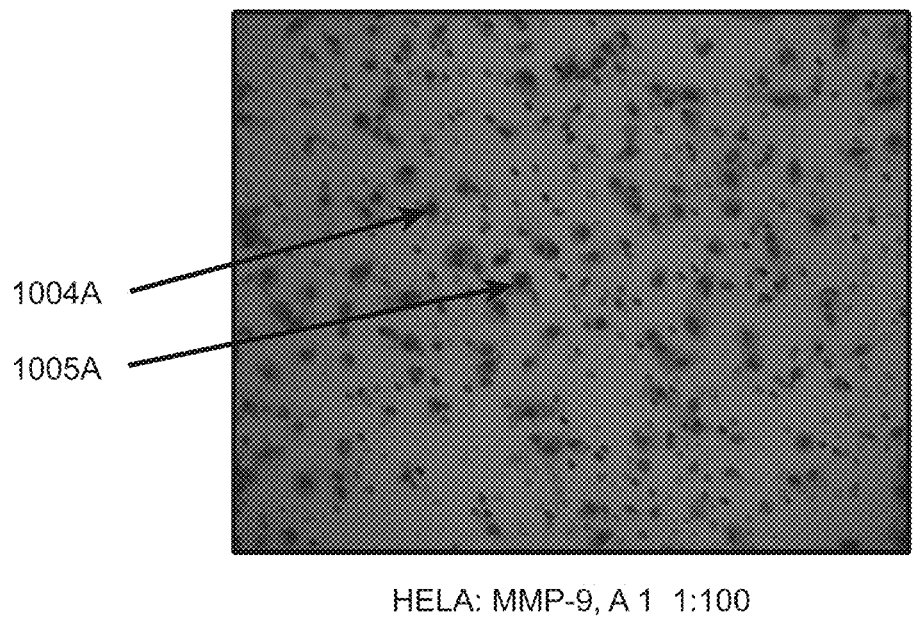
Figure 3B:
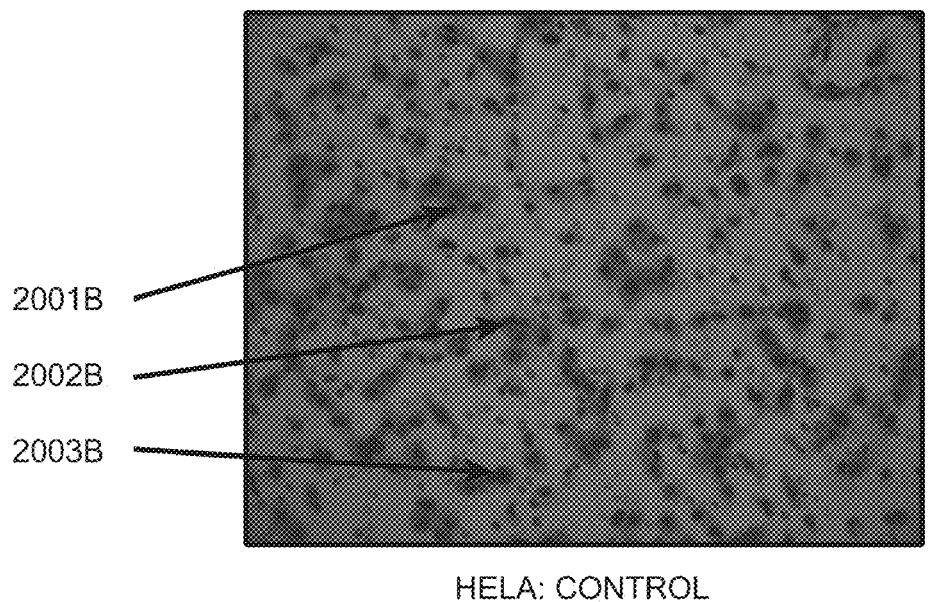
Figure 3B:
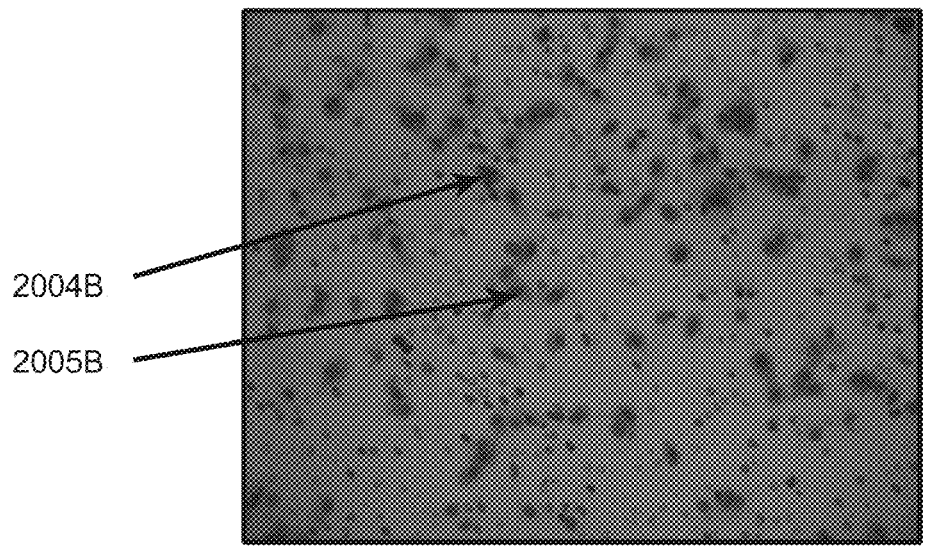
Figure 3C:
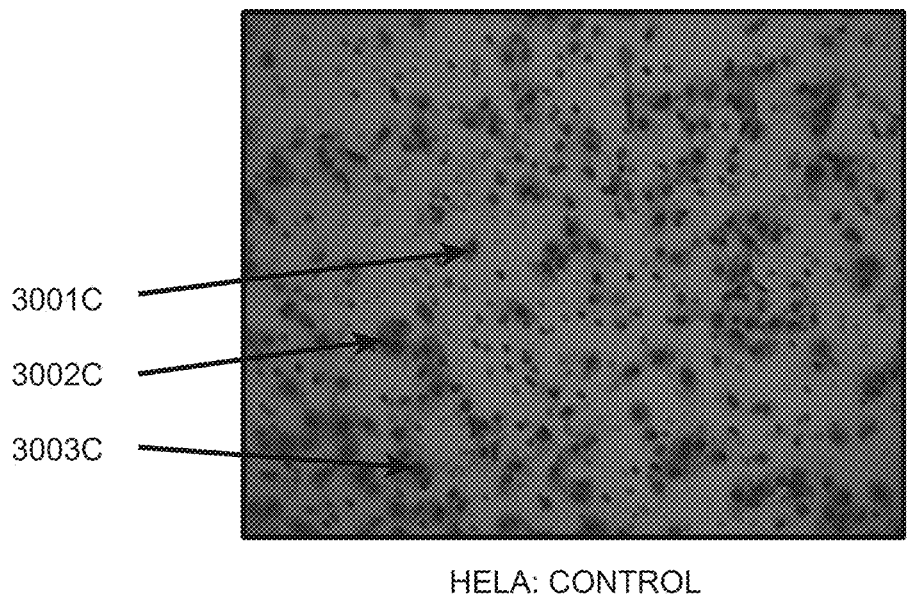
Figure 3C:
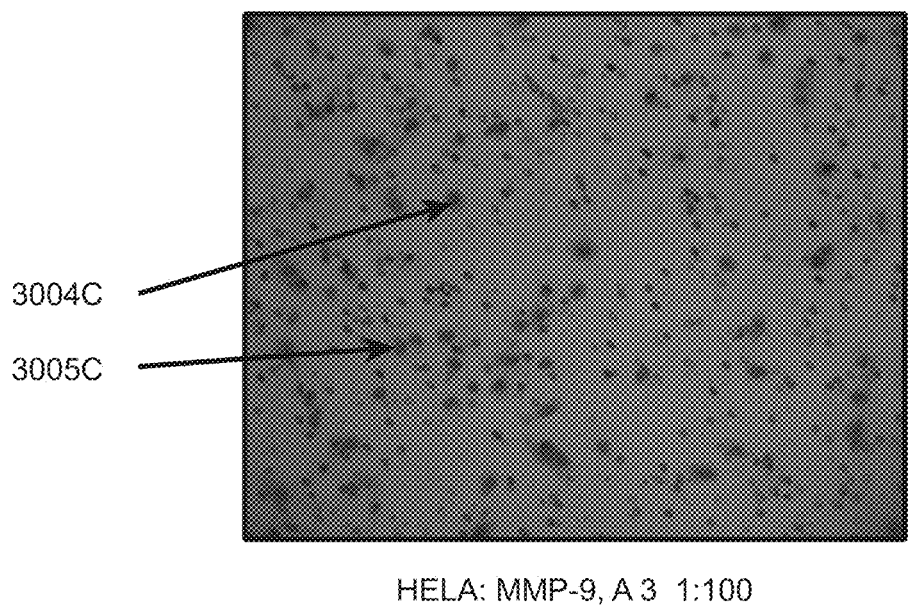
Figure 3D:
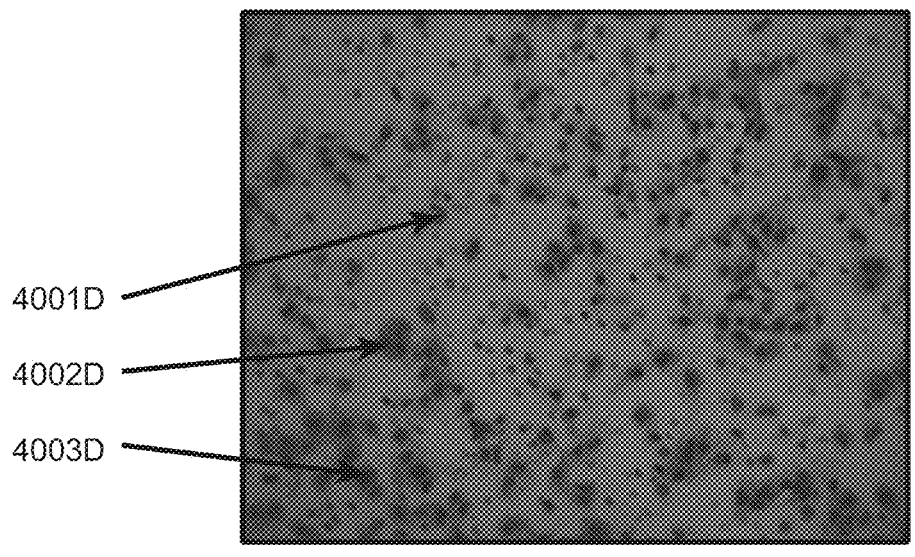
Figure 3D:
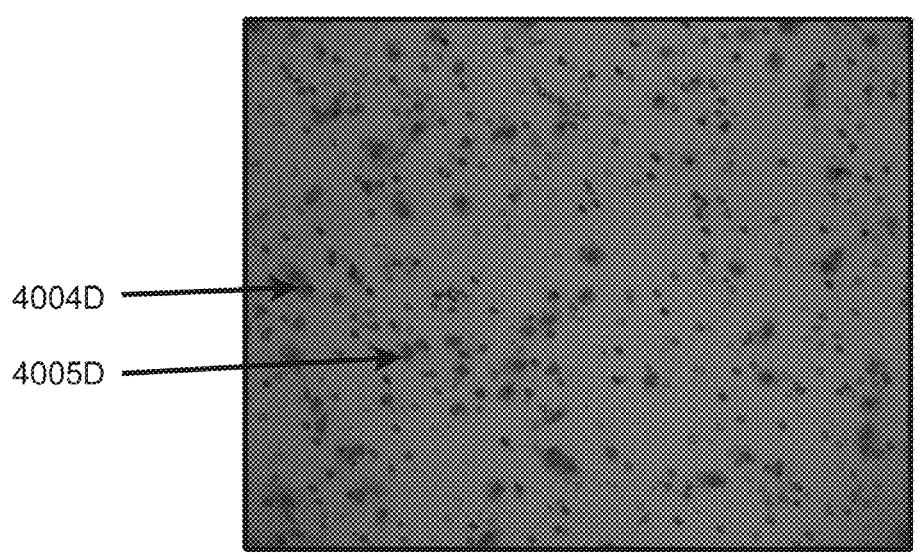

FIG. 2 explains the current disclosure in steps of vaccine production and immunization 200. Identification and design of the MMP's are carried out 210 using the MMP sequences. Oligopeptides are synthesized 220 and represented by synthetic oligopeptides 240. The formulate oligopeptides for vaccination are 222. The antibodies are produced as shown in 226. The mice 242 are immunized 224 using vaccine with syringe 240. The oligopeptides may be of specific length. Several permutations and combinations of the sequences were tested. The instant disclosure sequences are shown in para [0007] as MMP-9 A1-3 and MMP-2 A4. Prior to the selection of these four sequences as potential oligopeptides, several potential binding sites for MMP-9 and MMP-2 were identified. A total of eight oligopeptides were synthesized and tested using fibrosarcoma HT-1080 cell line and cervical cancer cell line DoTC-2. Only four sequences were selected to be pursued. The MMP-9 A1-3 and MMP-2 A4 were synthesized in a linear and circular format. Many modifications for these sequences were also done in one embodiment. The modifications were substituting one or more amino acid residues at N-terminal, C-terminal and both C and N terminals, substitution of amino acid residues based on similar charge and polarity, without consideration of charge and polarity, omitting of amino acids in C and N terminal, omitting only in C-terminal and only in N-terminal.

In another embodiment, substitution and omission may be carried out simultaneously. The oligopeptides may be further modified by repeating the sequences and combining more than one MMP-9 A1-3 AND MMP-2 A4 for producing and formulating a vaccine. The peptidomimetic to the MMP's may be used to block the binding site of an overexpressed MMP in a specific disease.

In one embodiment, the oligopeptide may be used as feedback regulators to specifically prevent or reduce the synthesis rate of MMP-9 and MMP-2 productions at the cellular level. In one embodiment process of blocking and inhibition of ECM destruction by antigens produced due to vaccination of mice.

In another embodiment, the synthesized oligopeptides were biotinylated at N-terminal using four carbon spacers by Genscript (Pitcataway, N.J. 08554 USA) and conjugated to KLH protein. In an experiment performed on mice animals were procured, immunized, tumor induced and observed for effectiveness of the treatment of oligopeptide-induced immunotherapy.

The injections were prepared using 100 µl l of KLH conjugated biotinylated peptides and 100 µl of complete Freund's adjuvant (Sigma, St. Louis, Mo.).

Male C57BL/6 mice 6 weeks of age on arrival were purchased from Simonsen Laboratories, Gilroy, Calif. and maintained in microisolator cage under pathogen-free conditions on a 12-h light/12-h dark schedule for a week. All animals were cared for in accordance with institutional guidelines for the care and use of experimental animals. After housing for a week, the mice (n=5/group) were immunized by intraperitoneal injection on Day 0, and incomplete Freund adjuvant (Sigma) on Day 7, 14 and 28. The blood samples were tested for their immune response by standard Elisa test using microtiter plates. Repeating injections of synthetic peptides in mice produce an immune response to specific individual peptides. Various dilutions were tried and examples of dilutions tried are 1:100, 1:1000 and 1:10000.

Conjugation of Peptides

All four peptides were conjugated covalently to keyhole limpet hemocyanin (KLH) protein. In a typical experiment 1 mg of the peptide, 4 mg of KLH was dissolved in 5 ml of 0.01 M $NaHCO_3$ and 2 µl of glutaraldehyde and stirred overnight. At the end 100 µl of 1M glycine ethyl ester to the final concentration of 0.1 M and left for 30 min at room temperature. Then precipitated with 4-5 vol of cold acetone at −70 C for 30 minute. Then briefly warmed at room temperature and pellet at 10,000 g for 10 min. The pellet was dissolved in 1 ml of 0.1M $NaHCO_3$ and stored at −20° C.

Anti-Peptide Immune Response Assay

Microtiter plates were coated with individual peptide in 100 µl/well 5 µg in mM carbonate buffer, pH 9.5 for 20 h at 20° C. After washing, wells were incubated with serial dilution of mouse serum in PBS/0.5% BSA, Tween™ 20 (binding buffer, BB). After washing, well were incubated with 100 µl/well rabbit anti-mouse IgG polyclonal antibody conjugated with horseradish peroxidase (HRP) in BB for 30 rain at 37° C. After washing, the titer of anti-peptide mouse IgG was determined by color reaction with TMB substrate solution at 450 nm.

At 1:100 dilution the intensity of immune response was higher for MMP-9 A 1-3 and slightly less for MMP-2 A 4 as shown in Table 1 below.

TABLE 1

| | Elisa - A1-A4 peptide | | | | | | | | | | | |
|---|---|---|---|---|---|---|---|---|---|---|---|---|
| | No Avidin | No Peptide | Non sp. pep cox | Cont Sera #3 | Test pep before B16FO given | | | | Test pep after B16FO given | | | |
| | 1 | 2 | 3 | 4 | 5 | 6 | 7 | 8 | 9 | 10 | 11 | 12 |
| CONT | | | | | | | | | | | | |
| 1:100 | .300 | .166 | .173 | .352 | .863 | .241 | .221 | .267 | .862 | 1.345 | .218 | .202 |
| 1:1000 | .149 | .443 | .158 | .215 | .339 | .174 | .164 | .286 | .699 | .234 | .166 | .164 |
| 1:10000 | .119 | .155 | .154 | .187 | .261 | .231 | .212 | .229 | .287 | .176 | .155 | .148 |
| MMP-9 A-1 | | | | | | | | | | | | |
| 1:100 | 1.248 | .336 | .362 | .418 | 3.898 | 3.868 | 3.843 | 3.895 | 3.897 | 3.864 | 3.820 | 3.87 |
| 1:1000 | .417 | .199 | .299 | .282 | 3.402 | 1.901 | 1.033 | 2.127 | 3.624 | 1.875 | .999 | 2.01 |
| 1:10000 | .146 | .210 | .227 | .244 | .394 | .274 | .228 | .330 | .645 | .244 | .226 | .22 |
| MMP-9 A-2 | | | | | | | | | | | | |
| 1:100 | .927 | .298 | .299 | .335 | 3.581 | 3.863 | 3.870 | 3.238 | 3.635 | 3.609 | 3.465 | 3.86 |
| 1:1000 | .208 | .210 | .189 | .242 | .646 | 1.339 | 2.856 | .360 | .526 | .859 | .277 | .274 |
| 1:10000 | .224 | .178 | .181 | .197 | .224 | .261 | .477 | .175 | .203 | .235 | .161 | .348 |
| MMP-9 A-3 | | | | | | | | | | | | |
| 1:100 | .706 | .626 | .339 | .285 | 3.775 | 3.810 | 1.991 | 3.812 | 3.776 | 3.814 | 2.063 | 3.84 |
| 1:1000 | .390 | .162 | .167 | .176 | .394 | 2.157 | .272 | 2.281 | .448 | 1.332 | .448 | 2.34 |
| 1:10000 | .123 | .142 | .151 | .158 | .159 | .631 | .159 | .267 | .167 | .209 | .158 | .296 |
| MMP-2 A-4 | | | | | | | | | | | | |
| 1:100 | .926 | .273 | .258 | .240 | 1.485 | 2.409 | 1.811 | 1.649 | 1.836 | 3.172 | 2.278 | 1.621 |
| 1:1000 | .340 | .162 | .162 | .192 | .650 | .974 | .771 | .289 | .7061 | .286 | .775 | .294 |
| 1:10000 | .148 | .142 | .150 | .179 | .220 | .257 | .208 | .168 | .290 | .313 | .230 | .167 |

The oligopeptide therapeutically effective amount may be administered to the mammal in many different ways and may not be limited to injections. The various methods of administration are well known in the art and some of the methods are described below.

A "mammal" to be treated by the subject method may mean either a human or non-human animal, such as mice, primates and vertebrates.

The specific diseases that would be target diseases for a treatment using MMP oligopeptide sequences and/or peptidomimetic are neoplastic diseases, inflammatory diseases, coronary artery diseases, occlusive cardiovascular diseases, degenerative diseases and infectious diseases. Some examples of neoplastic diseases may be, but not limited to, cancer, lymphoma, leukemia, and brain tumor. Some examples of inflammatory diseases may be, but not limited to, arthritis, asthma, atherosclerosis, Crohn's disease, colitis, dermatitis, lupus erythematous etc. Some examples of infectious diseases may include, but not limited to, are bacterial, viral, fungal, mycoplasmal, certain genetic diseases and other infections.

Drug formulations suitable for these administration routes can be produced by adding one or more pharmacologically acceptable carriers to the agent and then treating the mixture through a routine process known to those skilled in the art. The mode of administration includes, but not limited to, are non-invasive peroral, topical (example transdermal), enteral, transmucosal, targeted delivery, sustained release delivery, delayed release, pulsed release and parenteral methods. Peroral administration may be administered both in liquid and dry state.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions may also be administered as a bolus, electuary, or paste.

When an oral solid drug product is prepared, oligopeptide sequence of MMP and/or a peptidomimetic of the MMP's is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder, or capsules. Additives may be those generally employed in the art. Examples of the excipient include lactate, sucrose, sodium chloride, glucose, starch, calcium carbonate, kaolin, microcrystalline cellulose, and silicic acid; examples of the binder include water, ethanol, propanol, simple syrup, glucose solution, starch solution, liquefied gelatin, carboxymethylcellulose, hydroxypropylcellulose, hydroxypropyl starch, methyl cellulose, ethyl cellulose, shellac, calcium phosphate, and polyvinyl pyrrolidone; examples of the disintegrant include dried starch, sodium arginate, powdered agar, sodium hydrogencarbonate, calcium carbonate, sodium lauryl sulfate, monoglyceryl stearate, and lactose; examples of the lubricant include purified talc, stearic acid salts, borax, and polyethylene glycol; and examples of the sweetening agent include sucrose, orange peel, citric acid, and tartaric acid.

When a liquid drug product for oral administration is prepared, oligopeptide sequence of MMP and/or a peptidomimetic of MMP's is mixed with an additive such as a sweetening agent, a buffer, a stabilizer, or a flavoring agent, and the resultant mixture is processed through a routine method, to thereby produce an orally administered liquid drug product such as an internal solution medicine, syrup, or elixir. Examples of the sweetening agent include vanillin; examples of the buffer include sodium citrate; and examples of the stabilizer include tragacanth, acacia, and gelatin.

For purposes of transdermal (e.g., topical) administration, dilute sterile, aqueous or partially aqueous solutions (usually in about 0.1% to 5% concentration), otherwise similar to the above parenteral solutions, may be prepared.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). Formulations which are suitable for vaginal administration also include pessaries, tampons, creams, gels, pastes, foams, or spray formulations containing such carriers as are known in the art to be appropriate.

A targeted release portion can be added to the extended release system by means of either applying an immediate release layer on top of the extended release core; using coating or compression processes or in a multiple unit system such as a capsule containing extended and immediate release beads.

When used with respect to a pharmaceutical composition or other material, the term "sustained release" is art-recognized. For example, a therapeutic composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active salt and/or composition, for a sustained or extended period (as compared to the release from a bolus). This release may result in prolonged delivery of therapeutically effective amounts of any of the therapeutic agents disclosed herein.

Current efforts in the area of drug delivery include the development of targeted delivery in which the drug is only active in the target area of the body (for example, in cancerous tissues) and sustained release formulations in which the drug is released over a period of time in a controlled manner from a formulation. Types of sustained release formulations include liposomes, drug loaded biodegradable microspheres and drug polymer conjugates.

Delayed release dosage formulations are created by coating a solid dosage form with a film of a polymer which is insoluble in the acid environment of the stomach, but soluble in the neutral environment of the small intestines. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Alternatively, a delayed release tablet may be formulated by dispersing tire drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

A pulsed release-dosage is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

The phrases "parenteral administration" and "administered parenterally" as used herein refer to modes of administration other than enteral and topical administration, such as injections, and include without limitation intravenous, intramuscular, intrapleural, intravascular, intrapericardial, intra-arterial, intrathecal, intracapsular, intraorbital, intracardiac, intradennal, intraperitoneal, transtracheal, subcutaneous, subcuticular, intra-articular, subcapsular, subarachnoid, intraspinal and intrasternal injection and infusion.

Certain pharmaceutical compositions disclosed herein suitable for parenteral administration comprise one or more subject compositions in combination with one or more pharmaceutically acceptable sterile, isotonic, aqueous, or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic within the blood of the intended recipient or suspending or thickening agents.

When an injection product is prepared, oligopeptide sequence of MMP and/or a peptidomimetic of MMP's is mixed with an additive such as a pH regulator, a buffer, a stabilizer, an isotonicity agent, or a local anesthetic, and the resultant mixture is processed through a routine method, to thereby produce an injection for subcutaneous injection, intramuscular injection, or intravenous injection. Examples of the pH regulator or buffer include sodium citrate, sodium acetate, and sodium phosphate; examples of the stabilizer include sodium pyrosulfite, EDTA, thioglycollic acid, and thiolactic acid; examples of the local anesthetic include procaine hydrochloride and lidocaine hydrochloride; and examples of the isotonicity agent include sodium chloride and glucose.

Adjuvants are used to enhance the immune response. Various types of adjuvants are available. Haptens are used as adjuvants in this disclosure. Freund's adjuvants may also be used to produce water-in-oil emulsions of immunogens. Antigens in water-in-oil emulsions stimulate high and long-lasting antibody responses which can be attributed to the slow release of antigen. Antigens (preferably in saline) are typically mixed with an equal volume of the adjuvant to form an emulsion.

The phrase "pharmaceutically acceptable" is art-recognized. In certain embodiments, the term includes compositions, polymers and other materials and/or dosage forms which are within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the pharmaceutical compositions described herein are formulated in a manner such that said compositions will be delivered to a mammal in a therapeutically effective amount, as part of a prophylactic, preventive or therapeutic treatment.

In certain embodiments, the dosage of the oligopeptide compositions, which may be referred as therapeutic composition provided herein may be determined by reference to the plasma concentrations of the therapeutic composition or other encapsulated materials. For example, the blood samples may be tested for their immune response to their corresponding oligopeptides.

The therapeutic compositions provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

Expressed in terms of concentration, an active ingredient can be present in the therapeutic compositions of the present invention for localized use about the cutis, intranasally, pharyngolaryngeally, bronchially, intravaginally, rectally, or ocularly.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The most common routes of administration also include the preferred transmucosal (nasal, buccal/sublingual, vaginal, ocular and rectal) and inhalation routes.

In addition, in certain embodiments, subject compositions of the present application maybe lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

The therapeutic acceptable dosage may be combined with other drugs and may be treated as a combination drug.

In FIG. 2, the produced antibodies 241 are checked using ELISA. Innoculating the mice (228) was done using cancerous cells 246 by injection. The block of MMP's 230 by antigen 248 was observed. Intact ECM 234, shown as 250 by inhibiting ECM destruction 232 was demonstrated by in vivo and in vitro studies as discussed above and below.

Cancer Cell Lines and Culture

Human cervical cancer (Hela) and murine melanoma B16FO cells obtained from ATCC (American Type Culture Collection, Rockville, Md.) were maintained in Dulbecco's modified Eagle's medium supplemented with 10% fetal bovine serum and antibiotics. The media and sera used were obtained from ATCC, and antibiotics (penicillin and streptomycin) were from Gibco BRL, Long Island, N.Y.

Matrigel™ Invasion

Invasion studies were conducted using Matrigel™ (Becton Dickinson) inserts in 24-well plates. Suspended in medium containing anti-sera from the experimental immunized mice 1:100 dilution, human cervical cancer HeLa cells seeded on the insert in the well. The well has human dermal fibroblast primed media as chemotaxtant. The plates with the inserts were then incubated in a culture incubator equilibrated with 95% air and 5% $CO_2$ for 24 hours. After incubation, the media from the wells were withdrawn. The cells on the upper surface of the insert were gently scrubbed away with cotton swabs. The cells that had penetrated the Matrigel™ membrane were stained with hematoxylin and eosin (H&E) and visually counted under the microscope.

The inhibition was compared to the control. FIGS. 3A-3D show various matrix metalloproteinase oligopeptide and their effectiveness. There are many cells that are invading through the Matrigel™ compared to MMP-9 A1-3 and MMP-2 A4 exposed cells. For example, in FIG. 3A, cells numbered as 1001A-1003A are more in number compared to MMP-9 A1 treated cells 1004 A-1005A. Similar results are found for MMP-9 2-3 and MMP-2 A4 in subsequent figures.

The in vivo studies described above presented some interesting results in the form of weight of the mice, tumor weight, tumor burden studies and effectiveness of various oligopeptides used in a therapeutically effective amount to inhibit ECM digestion or destruction.

After dosing the mice, on $45^{th}$ day, mice were bleed through orbital puncture and blood was collected in 2-ml micro centrifuged tube. After testing for immune response against individual peptides, the mice in each group were inoculated subcutaneously with $0.5 \times 10^6$ in 0.2 ml PBS. After injection, the mice were returned the cages and fed regular Purina mouse chow diet. After four weeks, the mice were sacrificed and their tumors were excised. Dimensions (length and width) of tumors were measured using digital caliper, and tumor burden was calculated using the following formula: 0.5×length×width.

Figure 4:
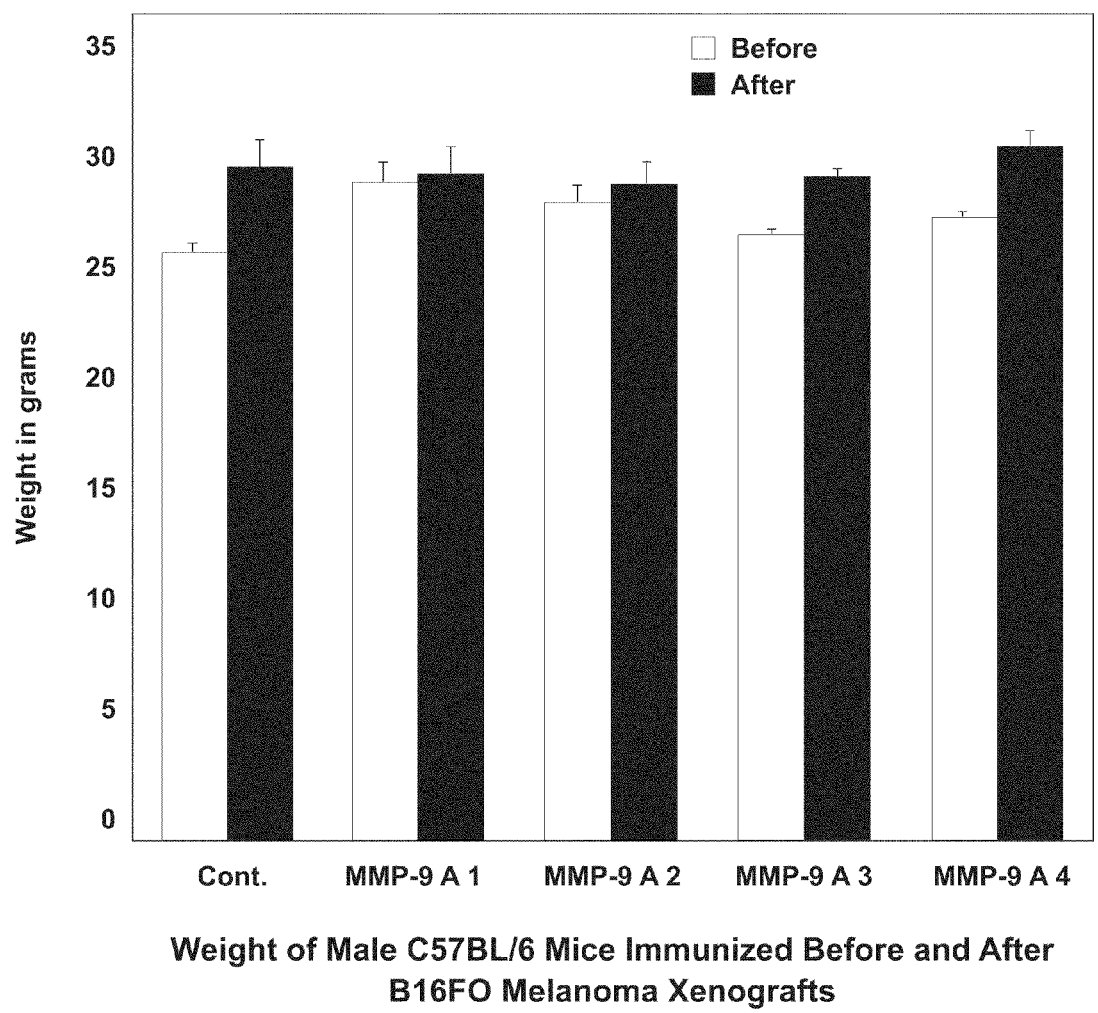
FIG. 4 illustrates the weight of the mice before and after the treatment.
Figure 5:
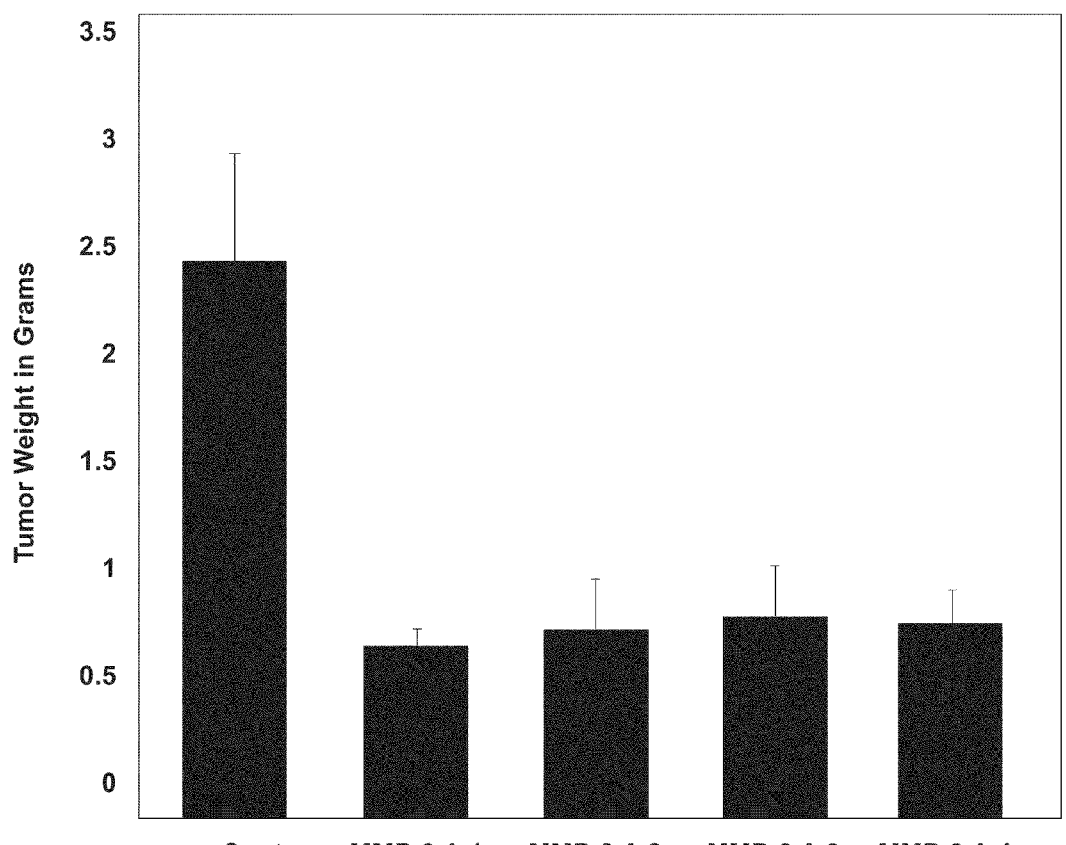
FIG. 5 illustrates an effect of immunization using matrix metallopeptidase MMP-9 A1-3 and MMP-2 A4 on tumor weight inhibition of melanoma cell line B16F0 xenografts in male C57BL/6 mice.
Figure 6:
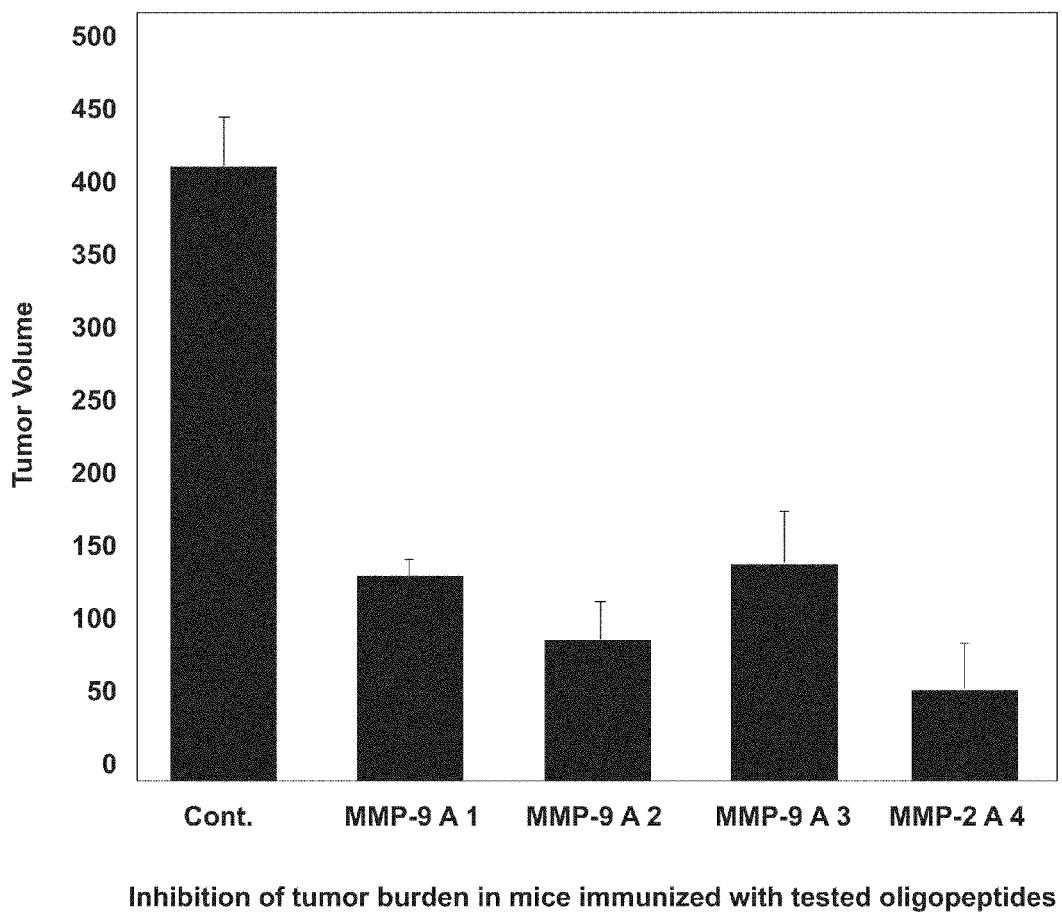
FIG. 6 is a view of the result tumor weight burden (length and width) on male C57BL/6 mice before and after the melanoma xenograft treatment.
Figure 7A:
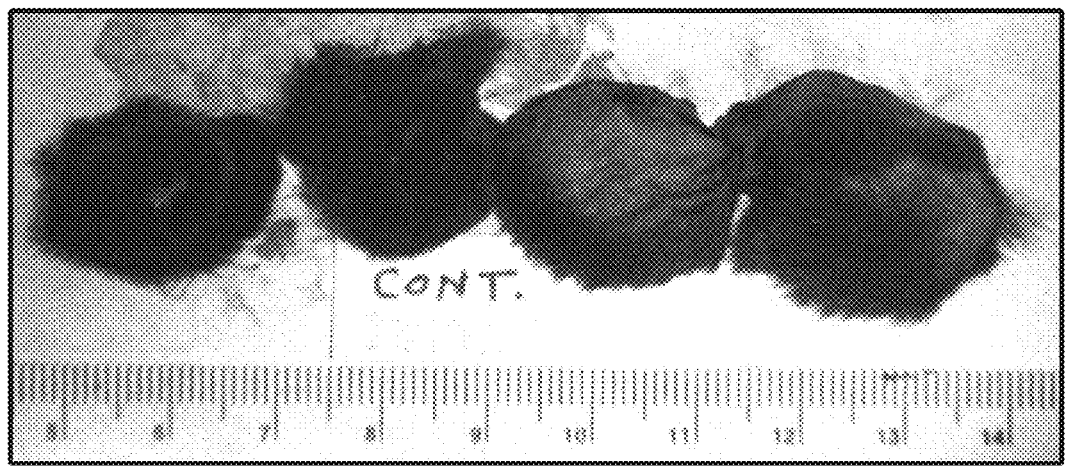
FIG. 7 A-E is a view of the tumor growth in control and tumor inhibition in immunized mice.
Figure 7B:
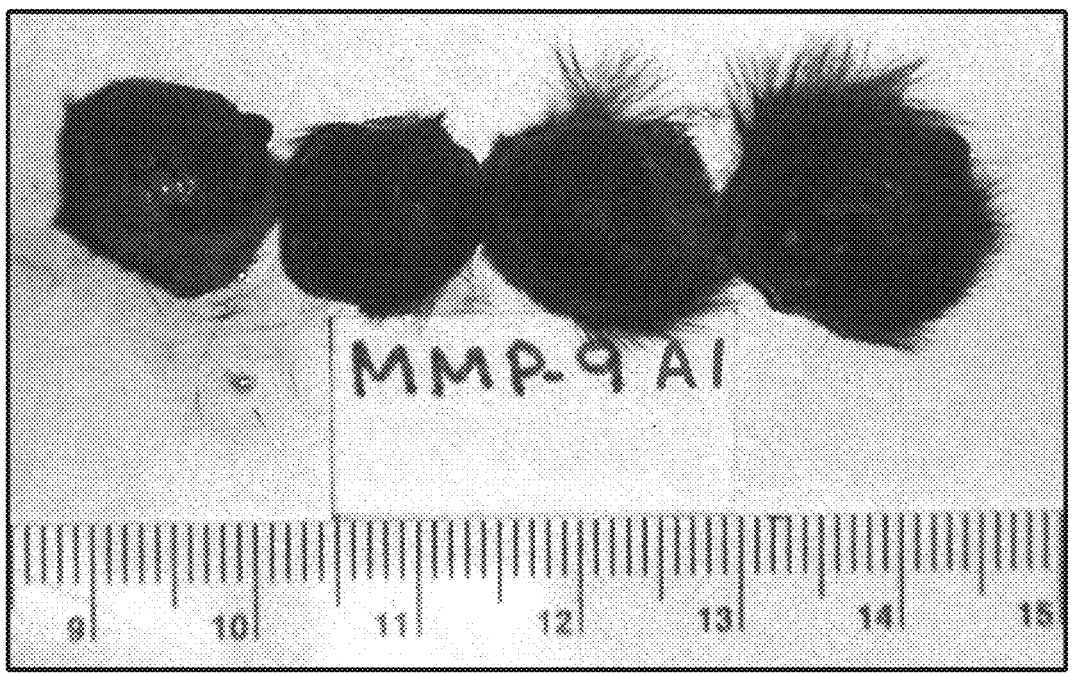
Figure 7C:
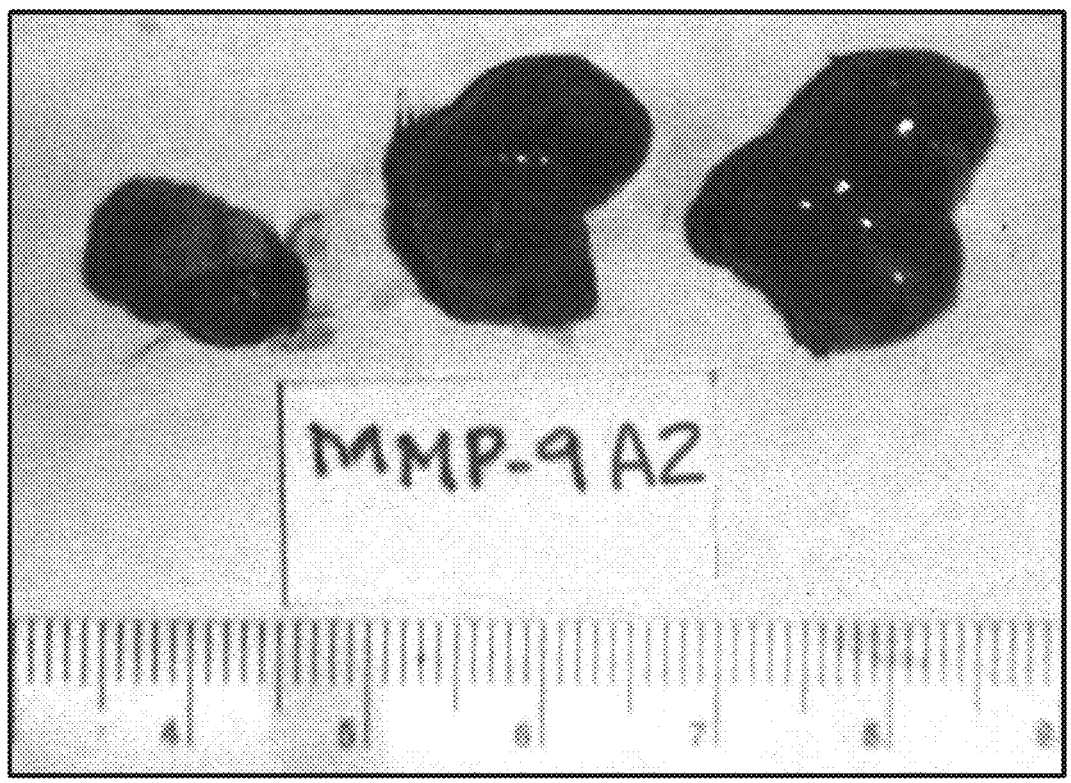
Figure 7D:
Figure 7E:
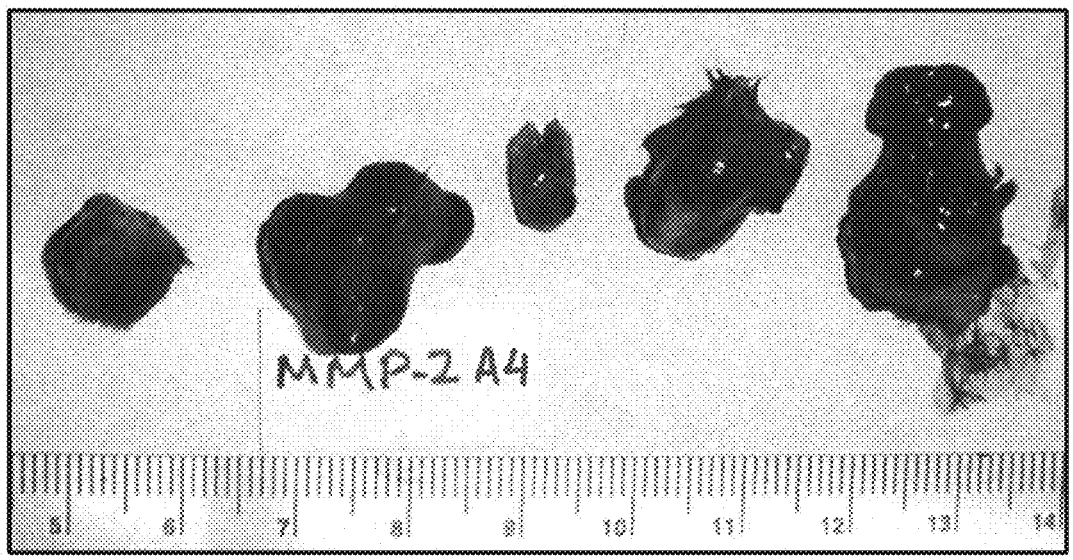
Figure 8:
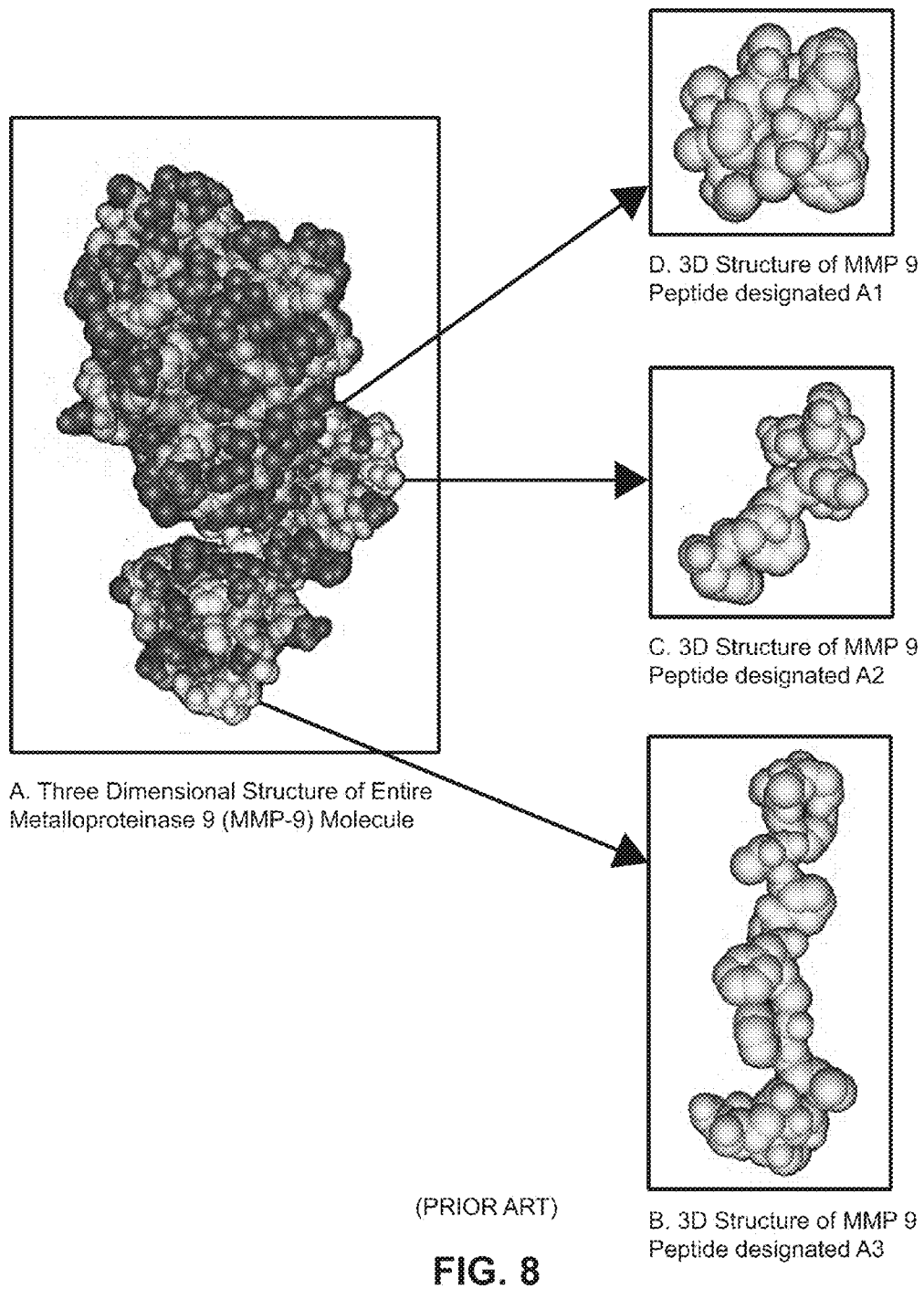
FIG. 8 shows a view of the binding sited for the various peptidomimetic on a MMP molecule.

The weight of the animals did not significantly change before and after treatment as shown in FIG. 4. FIG. 5 shows the therapeutic effect of all matrix metalloproteinase oligopeptide immunization effect on tumor weight. FIG. 6 shows the significant effect of tumor volume as compared to control tumors, further proving the effectiveness of the treatment method. FIG. 7 A-E visually shows some of the tumors excised and displayed. The significant reduction in size is very apparent. In one of the MMP-9 A 3 one of the tumors have completely disappeared. FIG. 8 shows a three dimensional structure of the MMP molecule. The figure also discloses the region of the molecule that enables MMP-9 A1, MMP-9 A2 and MMP-9 A3 in as a three dimensional structure. Peptidomimetic of these MMP may be designed based on the structure to inhibit MMP expression and prevent metastasis.

In addition, it will be appreciated that the various sequences, immunization processes, and methods of treatment disclosed herein may be embodied using means for achieving the various combinations of therapeutic dosage and delivery methods to treat a specific disease. Accordingly, the specification and drawings are to be regarded in an illustrative rather than a restrictive sense.

What is claimed is:

1. A peptide consisting of the amino acid sequence of SEQ ID NO: 2.

2. A peptide consisting of the amino acid sequence of SEQ ID NO: 3.

3. A peptide consisting of the amino acid sequence of SEQ ID NO: 4.

4. The peptide of claim 1, 2, or 3, which is biotinylated.

5. A conjugate comprising the peptide of claim 1, 2, or 3 covalently joined to keyhole limpet hemocyanin (KLH).

6. A pharmaceutical composition comprising one or more of the peptides of SEQ ID NO: 2, SEQ ID NO: 3, and SEQ ID NO: 4 and a pharmaceutically acceptable carrier.

7. The pharmaceutical composition of claim 6, wherein said one or more peptides is covalently joined to keyhole limpet hemocyanin (KLH).

8. The pharmaceutical composition of claim 6 further comprising an adjuvant.

9. A method of inducing an immune response against human matrix metalloproteinase-9 (MMP-9) in a mammalian subject, said method comprising administering to said subject an effective amount of a composition comprising one or more of the peptides of SEQ ID NO: 2, SEQ ID NO: 3, and SEQ ID NO: 4 to elicit the production of antibodies against MMP-9.

10. The method of claim 9, wherein said antibodies are effective to block the enzymatic activity of MMP-9 and inhibit tumor cell invasion.

11. The method of claim 9, wherein said mammalian subject is a human.

12. The method of claim 9, wherein said mammalian subject has an invasive tumor.

13. The method of claim 12, wherein the tumor burden of the mammalian subject is reduced.

14. A method for suppressing the growth of an invasive tumor in a mammalian subject, said method comprising administering to said subject an effective amount of the composition of claim 4 to elicit antibodies against human matrix metalloproteinase-9 (MMP-9) in the subject, wherein said antibodies are effective to block the enzymatic activity of MMP-9 and inhibit tumor cell invasion, thereby suppressing the growth of the tumor in the subject.

15. The method of claim 14, wherein the tumor burden of the mammalian subject is reduced.

* * * * *